(12) United States Patent
Eberlein (10) Patent No.: US 6,856,315 B2
(45) Date of Patent: *Feb. 15, 2005

(54) PAIN MIGRATION TRACKING AND DISPLAY METHOD

(76) Inventor: James B. Eberlein, Zsolna u 26/a, 1125 Budapest (HU)

( * ) Notice: Subject to any disclaimer, the term of this patent is extended or adjusted under 35 U.S.C. 154(b) by 401 days.

This patent is subject to a terminal disclaimer.

(21) Appl. No.: 09/888,787

(22) Filed: Jun. 25, 2001

(65) Prior Publication Data

US 2002/0030682 A1 Mar. 14, 2002

Related U.S. Application Data (63) Continuation-in-part of application No. 09/658,466, filed on Sep. 8, 2000, now Pat. No. 6,529,195.

(51) Int. Cl.[7] .............................................. G06T 11/20
(52) U.S. Cl. ..................... 345/440; 345/441; 600/557
(58) Field of Search ................................ 345/440–443; 705/2; 600/557

(56) References Cited

U.S. PATENT DOCUMENTS

| 5,692,500 | A | 12/1997 | Gaston-Johansson |
| 5,829,984 | A | 11/1998 | Kawai |
| 5,873,900 | A | 2/1999 | Maurer et al. |
| 5,908,383 | A | 6/1999 | Brynjestad |
| 5,938,690 | A | 8/1999 | Law et al. |
| 5,984,368 | A | 11/1999 | Cain |
| 6,018,675 | A | 1/2000 | Apkarian et al. |
| 6,044,303 | A | 3/2000 | Agarwala et al. |
| 6,529,195 | B1 * | 3/2003 | Eberlein ..................... 345/441 |

OTHER PUBLICATIONS www.pain.com.

www.phtcorp.com.

www.docucare.net.

* cited by examiner

Primary Examiner—Matthew Luu
(74) Attorney, Agent, or Firm—Banner & Witcoff, Ltd.

(57) ABSTRACT

A method of obtaining and displaying pain information from a user connected to a pain-tracking computer through a computer network is provided. The invention provides a system that allows users, and health care professionals to track the location and intensity of a patient's pain and the corresponding symptoms, lifestyle and medication usage over a period of time.

23 Claims, 10 Drawing Sheets

Registration

Please enter your name
▭ —302

Please enter a password
▭ —304

List the names of doctors who may review your data
1. ▭ —306a   3. ☐ more doctors —306c
2. ▭ —306b   4. ☒ no doctors —306d Please enter medical history information by selecting the following link
[ Medical History ] —308

Please setup your account by selecting the following link
[ Account Setup ] —310

Tabs: MAP | SYMPTOMS | LIFESTYLE | MEDICATIONS | REPORTS | SERVICES | RESOURCES

700

- ● Medication 1
- ○ Medication 2
- ○ Medication 3
- ○ Medication 4
- ○ Medication 5

Name of Medication:
- Percocet
- Percocet 5
- Percocet 7.5
- Lortab 5
- Lortab 7
- ----
- Birth Control Pills Number of times taken in past 24 hrs:
1
2
3
4
5 drop down menus

Comments:

Record Readings

HELP

PAIN MIGRATION TRACKING AND DISPLAY METHOD

This application is a continuation-in-part of U.S. application No. 09/658,466, entitled "Pain Migration Tracking and Display Method" and filed Sep. 8, 2000, which is now U.S. Pat. No. 6,529,195, the entire disclosure of which is hereby incorporated by reference.

FIELD OF THE INVENTION

The present invention relates to the field of pain management, and to a tracking and monitoring process for people with acute or chronic pain conditions. More specifically, the present invention provides a system that allows patients and health care professionals to track and monitor the physical location and intensity of a patient's pain, along with a range of A corresponding information such as symptoms, lifestyle changes, the effectiveness of medical intervention, etc. important in the assessment and diagnosis of pain conditions.

BACKGROUND OF THE INVENTION

In the past, pain was considered outside the realm of medicine because of its subjective nature, and often ignored and left untreated. This outlook has changed in recent times, and now the assessment and treatment of pain has become an integral part of medical practice. In the US this fact is evidenced by guidelines put forth in 1999 by the Joint Commission on Accreditation of Health care Organizations (JCAHO), calling pain the "fifth vital sign," and in federal legislation making 2001–2011 the "Decade of Pain Control and Research."

While research has shown that patient self-report instruments are an economical and reliable means of assessing a person's pain condition, the means for doing this has generally been limited to handwritten diaries. With or without handwritten diaries, diagnosing and treating patients with pain disorders involves sorting through and evaluating large amounts of information. Typically a health care professional asks a patient a series of questions to help diagnose the problem and may record certain information on a diagram of the human body. When a patient experiences different degrees of pain over a given period of time it can be time consuming for the health care professional to record all of the information. In addition to consuming a large amount of time, it can be difficult for the health care professional to effectively analyze all of the information collected.

As the amount of information provided to a health care professional increases, so does the probability that the health care professional will overlook relevant symptoms or fail to recognize a correlation between a symptom and other information provided to the health care professional. As a result, the health care professional may order the patient to undergo tests that would not otherwise be necessary. Unnecessary tests can be expensive and prolong the time period in which a patient suffers from pain.

For the patient, it is difficult to recall the exact nature and location of pain, particularly if its occurrence happens over a long period of time. Specific periods or moments may be recalled, but details of its occurrence (e.g. time, date, place), and variables (e.g. symptoms, lifestyle changes, medications) associated with it, before, during and after the occurrence of pain may go unreported. Accordingly, there exists a need in the art for a system that allows physicians and health care professionals to efficiently obtain pain information from patients (along with medical records) and that helps analyze and accurately display the obtained information in a manner that is meaningful to the user and/or the user's physician or health care professional. There also exists a need in the art for a system that allows individuals to efficiently provide such pain information and corresponding medical information.

SUMMARY OF THE INVENTION

The present invention provides a system that allows patients to record information such as the location and intensity of pain, and related information of value in assessing and diagnosing acute and chronic pain conditions. The information provided by the end-user patient can be in accordance with established medical standards and designed to help the patient better understand and control their pain condition, as well as to assist their health care professional in assessing and diagnosing it.

Additionally, the system can serve as a real time tool for patient monitoring, and for sending and managing alerts and alarms, and other forms of communications between patients and their health care professionals.

The obtained information can be displayed chronologically in pictures to the patient, and their health care professional, and illustrate in video and graphical form the location and intensity of the patient's pain, and related information (symptoms, lifestyles, medications), over time. For the benefit of medical research, health care professionals, and others, with an interest in analyzing the effectiveness of treatment and medical intervention, the present invention can also allow information on patient groups, or entire populations of patients, to be analyzed and illustrated graphically, in a manner like that used by individual patients, as described above. In this way large amounts of data is organized, analyzed and put into visual representations for faster and more effective interpretation.

The advantages of the present invention can be provided by a method of obtaining and displaying medical information. The medical information may include the location and intensity of pain experienced as well as corresponding symptom, medication and lifestyle characteristics. The method includes the steps of receiving from a user a first set of medical information by the user during a first time period and receiving from the user a second set of medical information by the user during a second time period. A health care professional or user can choose to display the information received in different formats accessible from several different locations through the use of a web browser or on a PC, handheld device or other devices used for communicating over the Internet, or like communication channels. In particular, the displayed formats may include charts, histograms and a moving sequence of images that shows changes in the recorded information over time. The data displayed can assist physicians and health care professionals in analyzing patient data, and could include feedback in the form of diagnostic considerations that would help medical professionals in conducting the proper tests used to diagnose a patient's condition. Additionally, the health care professional can set alarms within the invention, in order to be alerted when set limits (e.g. pain intensity, missed work days) are exceeded by their patient. This alarm could take the form of e-mail, page or a phone call to a predetermined address or number.

The full range of advantages and features of the invention are only appreciated by a full reading of this specification, and a full understanding of the invention. Therefore, to complete this specification, a detailed description of the

BRIEF DESCRIPTION OF THE DRAWINGS

The present invention is illustrated by way of example and not limited in the accompanying figures in which like reference numerals indicate similar elements and in which.

DETAILED DESCRIPTION OF PREFERRED EMBODIMENTS

Figure 1:
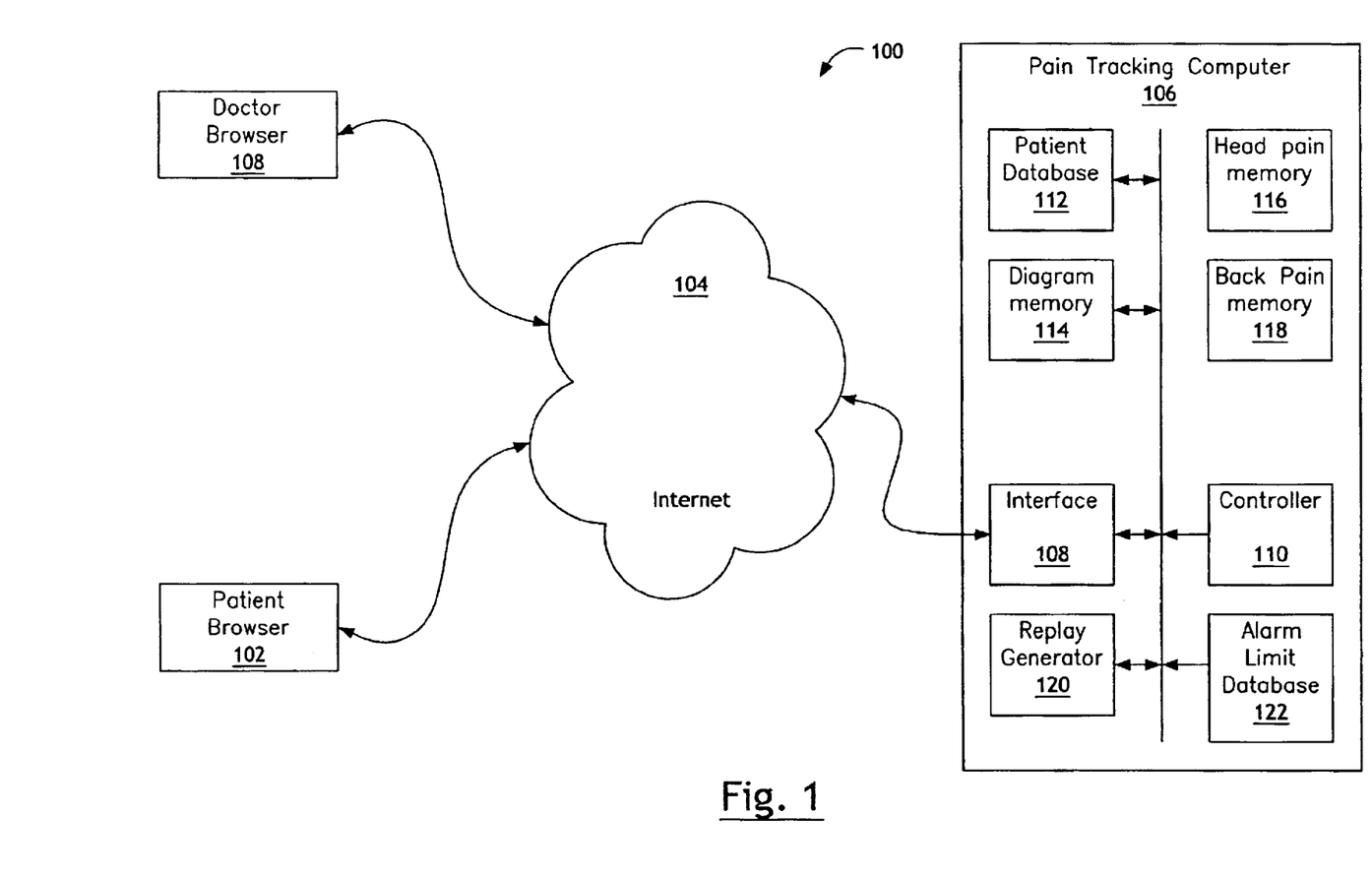
FIG. 1 shows a system for tracking and displaying pain in accordance with an embodiment of the invention.

FIG. 1 shows a system 100 for tracking and displaying pain in accordance with an embodiment of the present invention. A user enters information using a graphical user interface, such as through a conventional web browser 102. The entered user information travels through a computer network 104 to a pain-tracking computer 106. Computer network 104 can be any network used to connect computers together, such as the Internet. Pain tracking computer 106 contains an interface 108 for communicating with network 104 and a controller 110 for controlling the operation of the computer. The remaining modules shown in pain tracking computer 106 are described in detail below.

A health care professional can also send and receive information to and from computer network 104 via a different web browser 108. Examples of browsers that can be used with the present invention include Microsoft Internet Explorer and Netscape Communicator. Furthermore, browsers 102 and 108 can be installed on personal computers, personal digital assistants, cellular telephones or any other wireless communication devices used to access a computer network. A replay generator 120 links together time-sequenced images of pain locations on a graphical display in order to allow a health care professional to visually observe pain migration and intensity. The time-sequenced images can be viewed from the physician or health care professional's browser 108 or from another device.

Pain tracking computer 106 can also alert the health care professional, or user, when a predetermined condition exists. For example, a health care professional may want to be alerted when the user takes a medication for more than 3 days. An alarm limit database 122 can be located within pain tracking computer 106 and can store information relating to variables such as sleep, medication, and pain intensity and when an alert condition should be declared. Controller 110 may retrieve the information from database 122 and compare it to information provided by the user. The health care professional or user, or both, may receive alert messages by communication channels such as e-mail, pager or telephone. Furthermore, in one embodiment of the invention, the health care professional or patient may rank or provide conditions for receiving alerts through the communication channels. As an example, a health care professional may decide to first receive an e-mail message and to receive a page 2 hours later if the health care professional does not respond to the e-mail message. Of course, the health care professional or patient may also elect to be alerted of certain conditions by one communication channel and other conditions by other communication channels, or to have such alerts diverted to others individuals. The communication channel may be chosen to correspond to the urgency of the alert.

Figure 2:
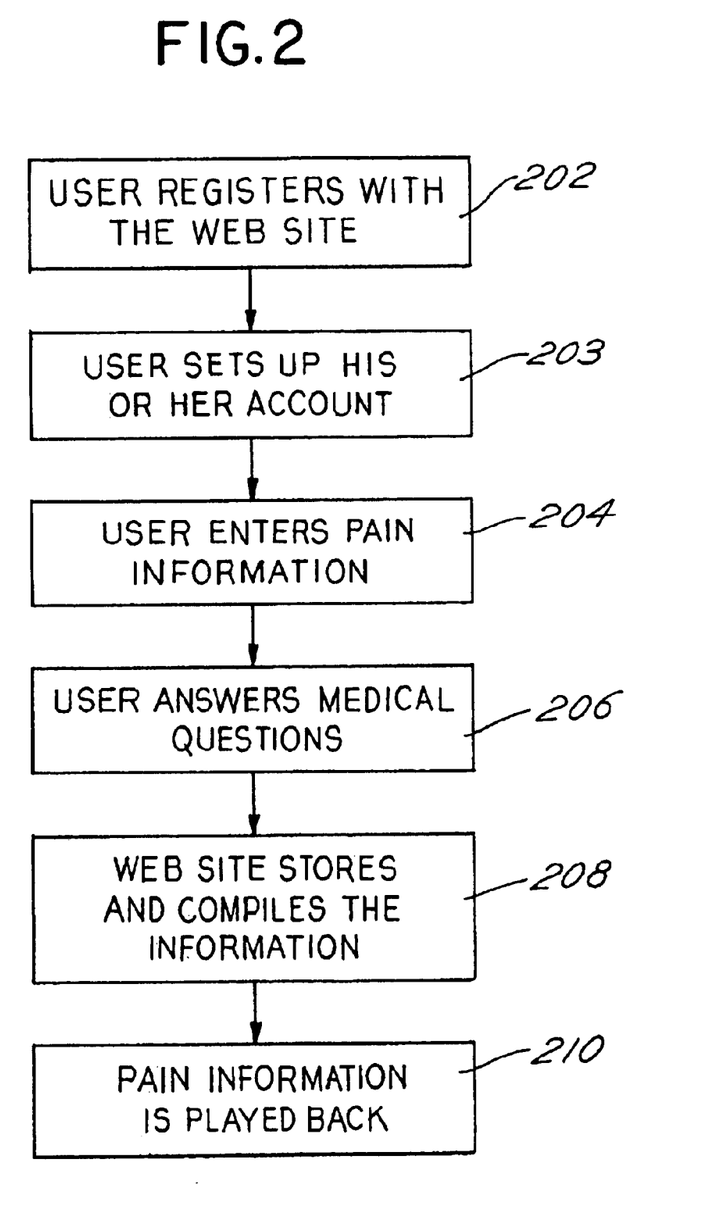
FIG. 2 shows a method for tracking and displaying pain in accordance with an embodiment of the invention.

FIG. 2 shows a method for tracking pain migration in accordance with a preferred embodiment of the invention. In step 202, the user registers via the web site, or is registered by a properly authorized individual. The registration step may also be accomplished by telephone (e.g., by speaking to an operator or to an interactive-voice-response type system); by entering information on a web page; or any other manner that allows pain-tracking computer 106 to obtain information from the user. The user may setup an account in step 203. In the setup step, the user can specify pain tracking selection criteria (medications, foods, moods, intercourse, etc.) as well as create user definable fields if desired. Alternatively, the selection criteria may be predefined by a health care provider, system operator or another party. The user can have their health care professional, or other authorized individuals, set up their account for them. The user may also set user preferences, such as links to family, friends and groups. Furthermore, the user may choose to share their information and join forums and register for other services.

In step 204, the user enters pain information graphically through a user interface that permits the user to identify variables such as the location, intensity and characteristics of their pain. In step 206, the user optionally answers questions regarding their lifestyle, symptoms and other questions that are specific to their treatment. In step 208, the pain information for the particular user may be collected across a sequence of different time periods (e.g., hours, days, weeks, months or years) and stored in a database. Of course, the database may be a secure database to protect confidential patient information. Replicate copies of the database may be produced for added security, backup or re-licensing and may require user consent.

Pain tracking computer 106 compiles the information provided by the user in step 208 and may also use algorithms designed to assist health care professionals with assessing and diagnosing a user's conditions. Finally, in step 210, the collected pain information is displayed for the user and/or their health care professional, or other authorized individuals or organizations, to review.

Computer-executable instructions for performing the method illustrated in FIG. 2 and the other disclosed methods may be stored on a computer-readable medium, such as a floppy disk or CD-ROM.

Figure 3:
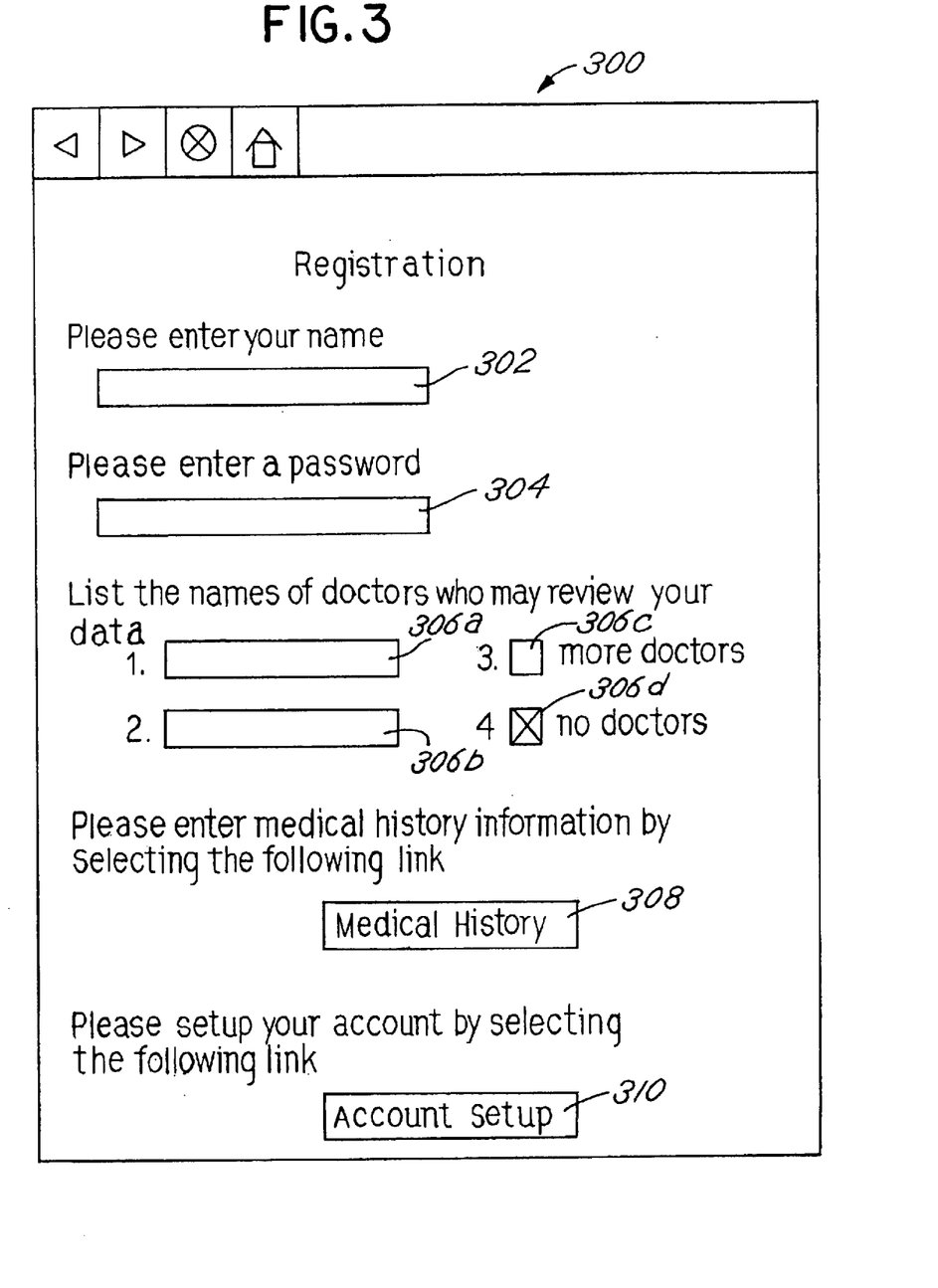
FIG. 3 shows a web page, or other graphical user interface, that a user or their health care professional or other authorized parties, can use to register with the pain mapping and tracking service.

FIG. 3 shows a web page 300 that allows a user, health care professional, or other authorized individuals or organizations to register with pain tracking computer 106. The user enters his or her name in block 302 and a password in block 304. The user may also provide a list of physicians or health care professionals who may access the information provided by the user. The physicians and health care professionals are listed in blocks 306a–306b. Box 306c may be selected to list additional physicians, health care professionals or other parties. Furthermore, box 306d may be selected when the user wishes not to allow any health care professional to access the information. Based on the user type (e.g. someone seeking medical assistance versus someone on disability leave), the user's health care professional(s), or other individuals or organizations, could define the information to be provided by the user, the frequency of input, and other aspects related to the use of the invention.

The user can also provide his or her medical history or information relating to condition and medical history by selecting button 308 and answering a series of questions. The questions (not shown) can elicit typical information that a user provides to a physician or health care professional. For example, the user may provide information relating to his or her age, weight, sex, and past medical problems and treatments. The user may also enter or provide medical history information from family members or others as defined by the user or his or her health care professional(s) or other individuals or organizations, as authorized by the user. Finally, link 310 may be selected to set up the user's account in the manner described above; the same link 310 may also be selected by health care professionals, or other individuals or organizations, for setting up their own account(s) or the account(s) of particular user(s), as authorized.

In one embodiment of the invention, the user can identify family members or specific groups or individuals who are registered with pain tracking computer 106. Pain tracking computer 106 may then use information provided by family members or specific groups or individuals when determining which questions to ask or what information to provide. Information provided by the user can be stored in database 112. Alternatively, sensitive user information can be stored locally on the device the user uses to connect to computer network 104 to protect the user's privacy. The private information can then be retrieved when it is needed by pain tracking computer 106. In one alternative embodiment, health care professionals, or other individuals or organizations, can carry out the steps described in this paragraph, in place of the user, provided they are authorized to do so.

In the embodiment of FIG. 3, the user registers with pain tracking computer 106 and, as part of setting up his/her account, selects whether or not to allow his/her health care professional, or other authorized individuals, to access the entered information. The user is not required to share his/her information with a health care professional and can keep all information confidential. In one alternative embodiment, the health care professional or other authorized individuals, initially registers with pain tracking computer 106 and determines which users may utilize the services offered by pain tracking computer 106. The user can then contact pain tracking computer 106 and verify that he or she is the person authorized by the health care professional, for example, to utilize the services offered by pain tracking computer 106. Physician or health care professionals might want to control access to pain tracking computer 106 to prevent people with whom they do not have a professional relationship from utilizing the services offered by pain tracking computer 106.

Users registered with pain tracking computer 106 who have selected, either individually or through their health care professional, to have their information shared with their health care professional or other authorized parties can be listed, tracked, and updated on computer 106 in order to allow the health care professional or other authorized parties to better follow the user's condition.

Figure 4:
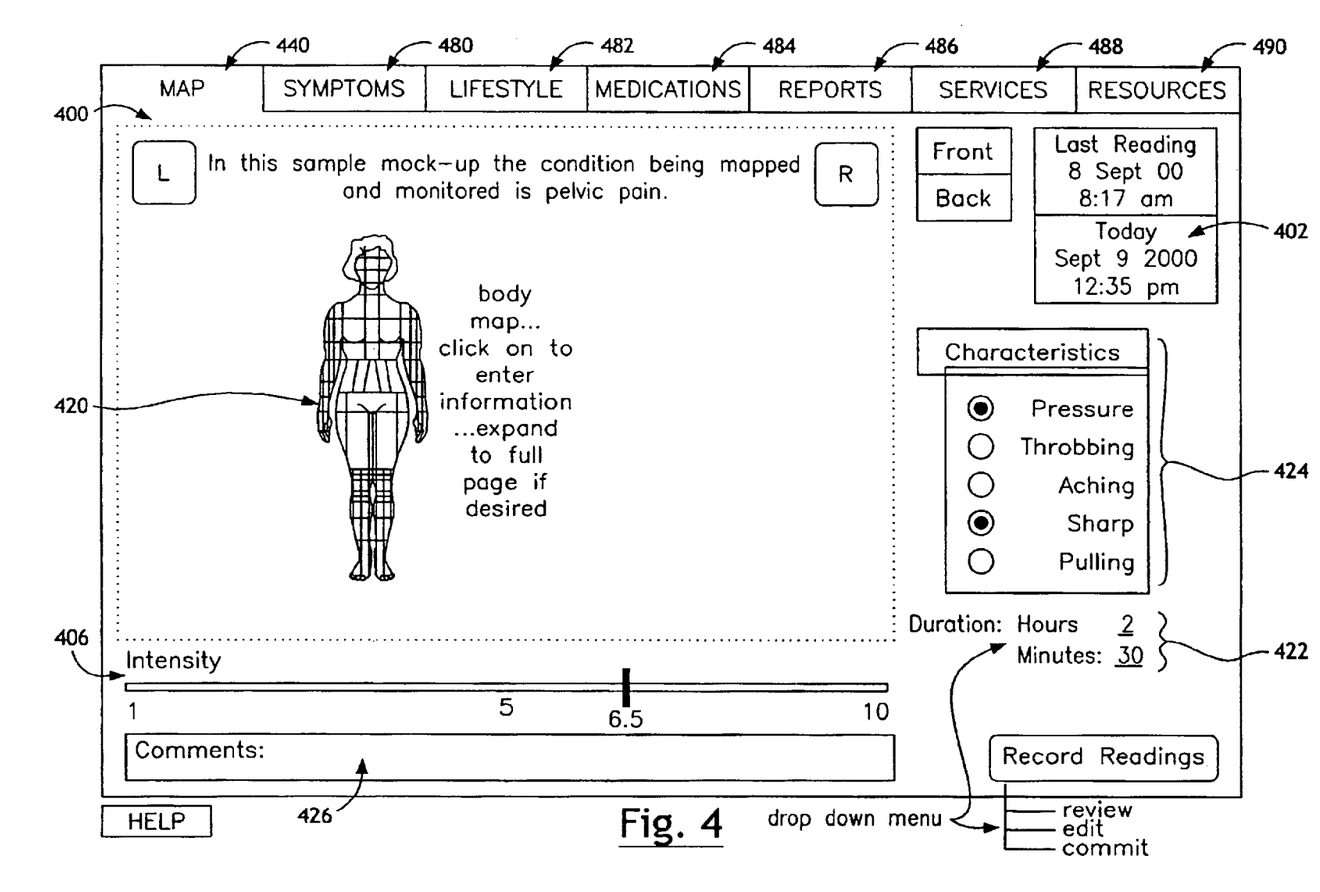
FIG. 4 shows a user interface in the form of a web page, or other graphical user interface, that can be used by a patient to enter pain and related information.

FIG. 4 shows one graphical user interface in the form of a web page 400 that can be used to enter pain information. The user, after entering the correct password and gaining access to the system, can enter the date and time corresponding to the information he/she is entering in text box 402. As a default, the user's computer will automatically record the current date and time as the date and time of the pain readings entered or other information input by the user.

Pain information may be entered by first selecting body map diagram 420 which may expand into a full-page graphical representation of the human body, or sections of the body, represented in different forms (e.g. skeletal, neurological, muscular system with tendons, simple wire diagram, solid models) or any combination of forms. FIG. 4 shows a body map diagram 420 corresponding to a female body. The sex of the diagram can be chosen based on the medical information provided by the user, as defined by the user or someone authorized on behalf of the user, at the time of registration and/or when the accounts is set up or its preferences modified by the user or an individual authorized to act on behalf of the user. Furthermore, pain-tracking computer 106 may store several different diagrams in diagram memory 114 and select a diagram based on the user's sex, weight and height. Several diagrams including front, back, side and 3 dimensional views, all in various sizes and forms, can also be used in place of diagram 420. The body map diagram 420 is divided into a plurality of different discrete elements (boxes or pixels), of various sizes and resolution, represented by wire frame grid like marks. In the preferred embodiment, diagram 420 is divided into uneven areas, although the invention is not limited in this respect. The size and shape of the grid areas may be a function of the structure of the human body. For example, an area may correspond to the shape of a muscle that could be the source of pain.

According to one aspect of the invention, the user graphically indicates one or more areas on the body map 420 in which the user is experiencing pain. Furthermore, in one variation of the invention, after selecting one or more areas on the body map 420, body map 420 may be replaced with another diagram (not shown) that illustrates the selected area in greater detail with another overlying grid. Greater detail may be required for portions of the body that contain small structures that are could be the source of pain. In another alternative embodiment, the user can position a cursor over the body map 420 and draw a shape that corresponds with the region of the user's body that is experiencing pain. The grid area(s) selected by the user are highlighted and may be stored in a memory of pain computer 106 for later use.

The user can select multiple areas on the body map in which he/she is experiencing pain. For each selected area, the user can slide the intensity bar to the corresponding pain intensity level in area 406. The corresponding area selected in body map 420 can be color-coded with each pain intensity level having a corresponding color, so that one can look at the diagram and determine the degree of pain experienced by the user in each area. The user can either click on the intensity bar or slide the intensity scroll bar indicator (406a) to the appropriate position to enter a pain intensity reading. In alternative embodiments, other features such as different textures or patterns may be used to distinguish between pain intensity levels.

To better quantify pain readings, standardized test, such as the SF36 or the McGill questionnaire (developed by Ronald Melzack PhD at McGill University), can be set to activate automatically at defined time intervals as defined by the health care professional, or other authorized individuals or organizations. Such tests ask the user a series of questions designed to obtain a complete assessment of the user's pain condition, both from a clinical perspective and as pertains to the user's quality of life and overall wellness/health. Furthermore, in one variation of the invention, standardized test can be modified or replaced by customized tests which either the user or a health care professional, or other authorized individuals or organizations have prepared.

After entering the pain intensity, the user can enter the duration of the pain in area 422 and the corresponding characteristics 424 for each of the pain areas the user indicated. The characteristics presented to the user can vary depending upon the pain conditions being tracked or as defined by the user, their health care professional, or a properly authorized individual or organization. Such characteristics may include: pressure, throbbing, aching, sharp and pulling. If the user is experiencing pain in more than one area, the user may select to repeat the steps defined above, as pertains to FIG. 4, and enter new information for each of the other areas that were selected in the body map 420.

Web or computer application page 400 may also include a link to a computer or web generated page that guides a user through a series of questions corresponding to the information added on page 400. The answers to the questions are designed to assist the user, their health care professional, or a properly authorized individual or organization with assessing, diagnosing and treating the user's pain condition. For example, if pain is indicated for an area frequently associated with sports injuries, the questions can be focused on likely sports activities (e.g., tennis, bicycling, or the like) that are frequently associated with a relevant type of injury that causes pain. The questions can relate to previous injuries, types of food consumed by the user or any other question that may illicit information to help diagnose the problem.

Questions can be stored in one or more memories located within pain tracking computer 106. As shown in FIG. 1, for example, questions related to head pain can be stored in a first memory area 116 and questions related to back pain can be stored in a second memory are 118. Obviously questions relating to other areas of the body can be included.

The present invention is particularly useful for diagnosing pain that migrates from one part of the body to another, such as pelvic pain. If a female user indicates that she is experiencing pelvic pain, the user may be presented with questions similar to those found on the Pelvic Pain Assessment Form distributed by the International Pelvic Pain Society. Such questions include "do you experience pain in your groin area when lifting" and "do you experience deep vaginal pain with sex." Finally, any additional information can be entered by the user in the comment field 426.

FIG. 4 also contains links to multiple other web pages in which a user can enter data or through which the user, or their health care professional, or other authorized individuals or organizations can receive information. These links can be designed to be part of a common template so that navigation within the system remains efficient. In one embodiment, the following links are located at the top of each of the web pages: 1) link 440 links the user with web page 400 that allows the user to enter pain information, 2) link 480 links a user with a web page 500 (shown in FIG. 5) that allows a user to enter symptom information, 3) link 482 links a user with a web page 600 (shown in FIG. 6) that allows a user to enter lifestyle information, 4) link 484 links a user with a web page 700 (shown in FIG. 7) that allows a user to enter medication information, 5) link 486 links a user with a web page 800 (shown in FIG. 8) that allows a user to view reports, 6) link 488 links a user with a web page 900 (shown in FIG. 9) that allows a user to get information on services, and 7) link 490 links a user with a web page 1000 (shown in FIG. 10) that allows a user to receive information on additional services available.

Figure 5:
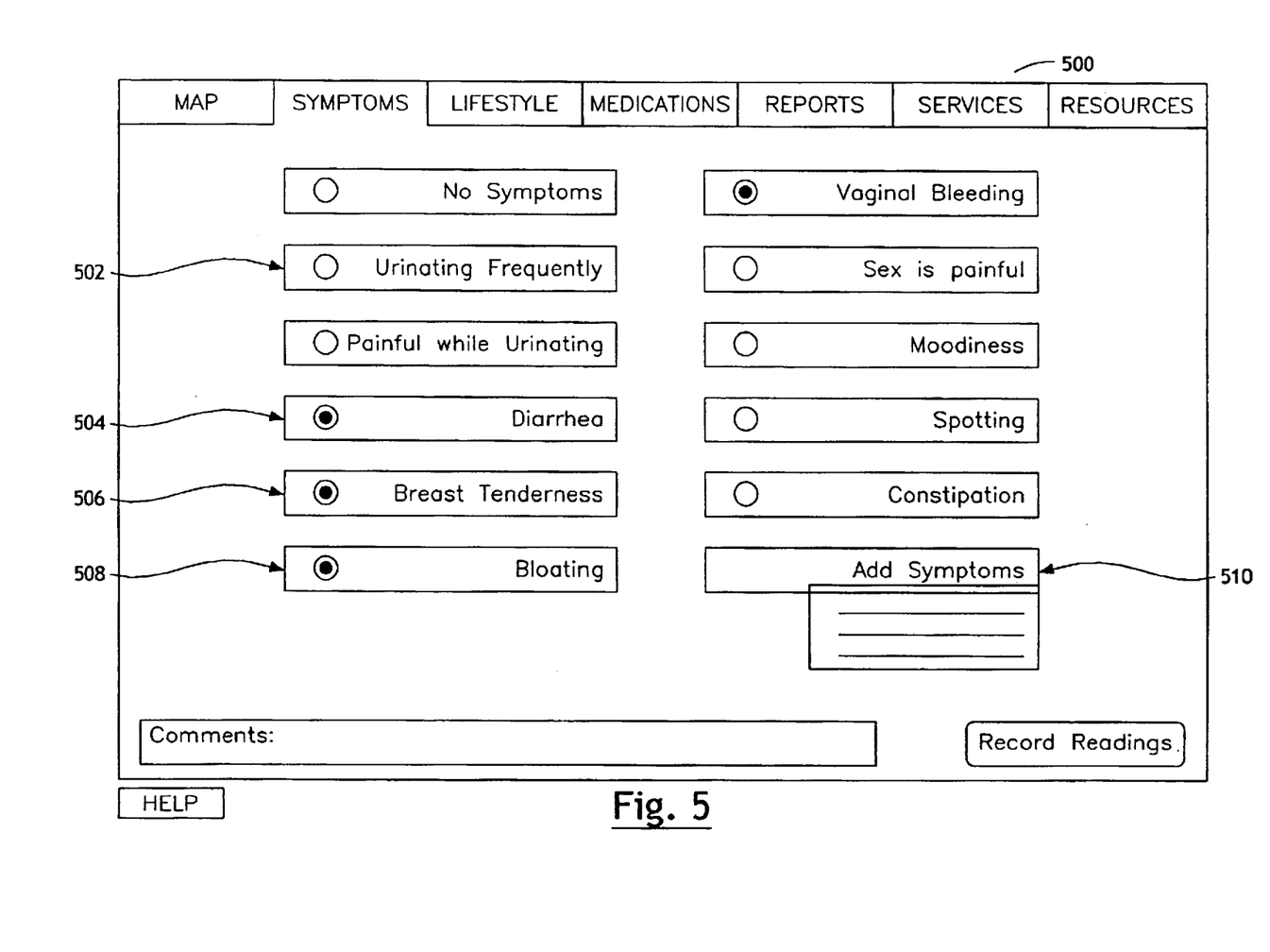
FIG. 5 shows a web page, or other graphical user interface, that collects information on a user's symptoms.

FIG. 5 shows a web page 500 that is presented when the user selects symptoms link 480. Web page 500 collects information from a user relating to overall symptoms that a user may experience. For example, in the case of pelvic pain, the patient can record urinary frequency 502, diarrhea 504, breast tenderness 506, and bloating 508. The user can enter additional symptoms in text box 510 and comments in text box 512. These symptoms, along with the pain characteristics entered, can be analyzed by a health care professional or other authorized individuals or organizations to assess a patient's condition.

Figure 6:
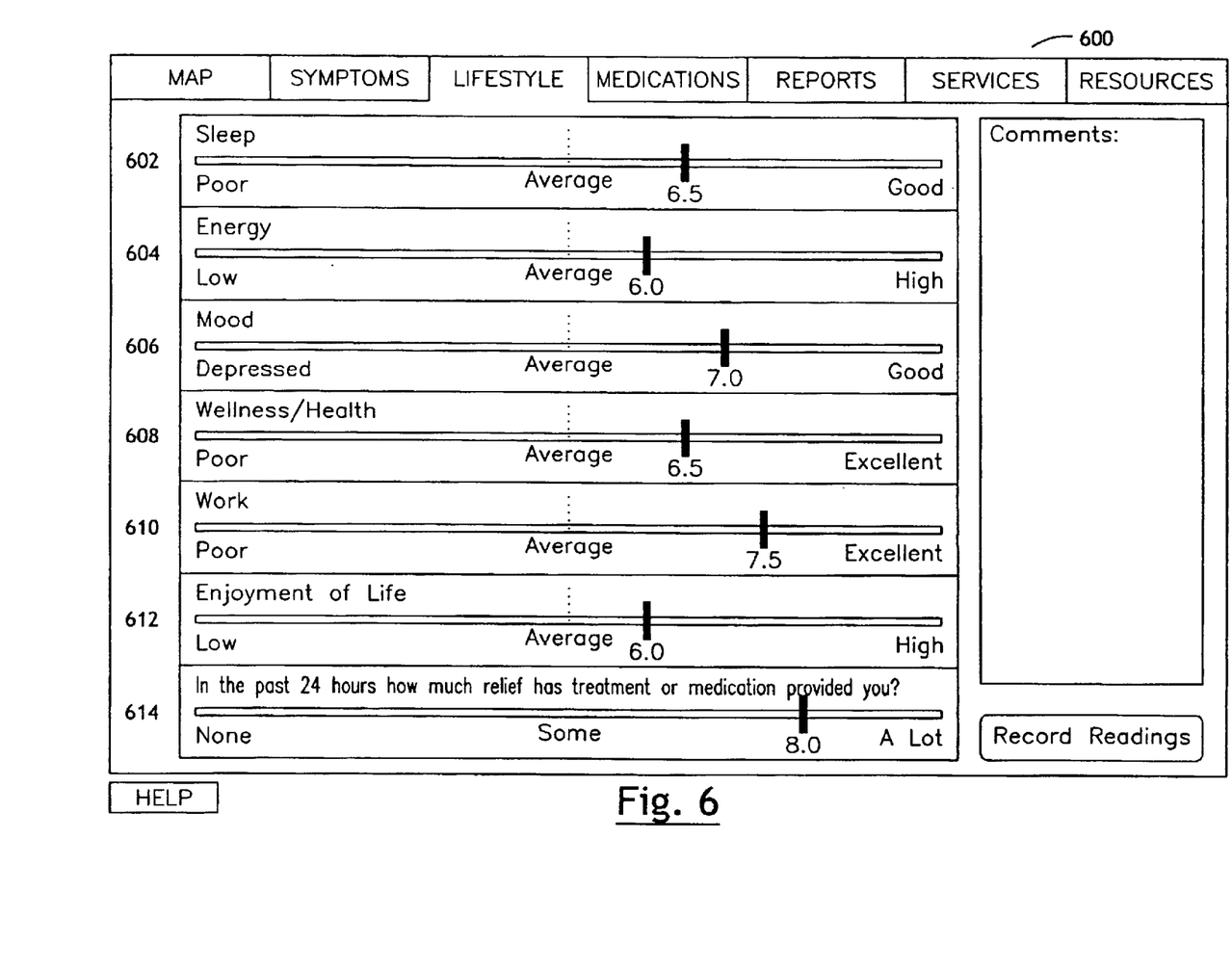
FIG. 6 shows a web page, or other graphical user interface, that collects information about a user's lifestyle.
Figure 7:
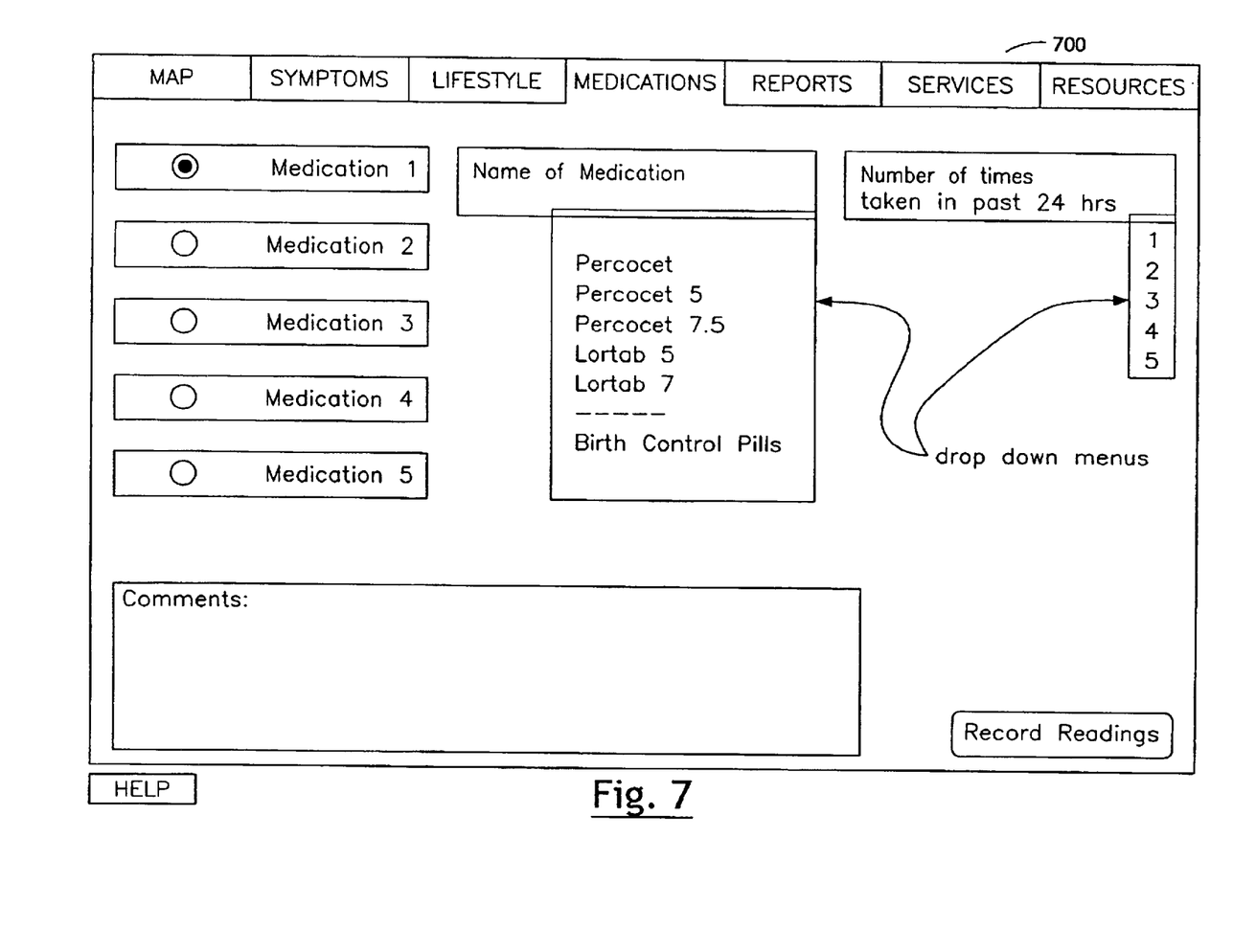
FIG. 7 shows a web page, or other graphical user interface, that collects information on the medications being taken by a user.

FIG. 6 shows a web page 600 that may be used by a health care professional, or other authorized individuals or organizations to collect patient lifestyle information that can help with assessing and diagnosing the patient's condition. A number of categories relevant to a patient's condition can be tracked and could include: sleep 602, energy 604, mood 606, wellness/health 608, work 610, enjoyment of life 612, and effectiveness of treatment and medication 614. For each selected category, the user can slide the rating bar to the corresponding rating level. As an alternative to sliding the rating bar, the user can click on the rating bar at the appropriate position to indicate their rating. FIG. 7 shows a web page 700 that includes a medication tracking system to help patients manage their regiment of medications. A patient can enter their medications, dosage amounts, and the time of day they administered each dosage. This data can be used to ensure that a patient is taking the appropriate medication in the manner prescribed by their health care professional, or other authorized individuals or organizations. The user's health care professional, or other authorized individuals or organizations may set a limit on any individual medication or on a combination of medications. If these limits are exceeded, a notification may be sent to the health care professional, or other authorized individuals or organizations. In particular, the notifications could be in the form of email, page, phone call or any other type of communication media. The notification could be tiered where first an email is sent followed by a page if the condition exists for a specific amount of time. The present invention provides rules within its application that will allow users, health care professional, or other authorized individuals or organizations to configure a wide (and virtually unlimited) range of notification settings that apply to the type of message, the sender, receiver(s), frequency, conditions, level of urgency, and the medium(s) for transmission, storage, forwarding and follow-up action, if any, required on behalf of the sender or one or more recipients.

Figure 8:
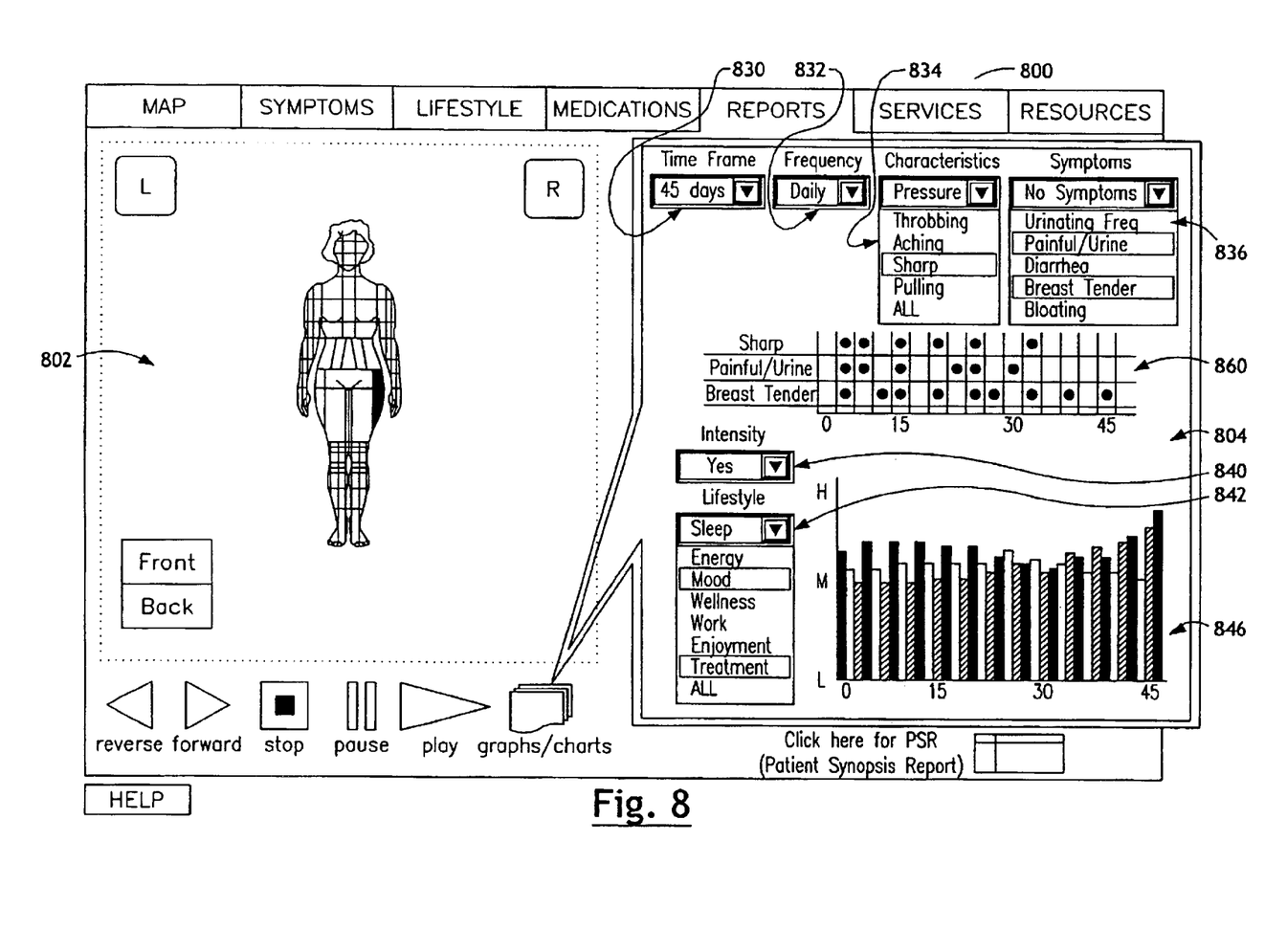
FIG. 8 shows a web page, or other graphical user interface, representing the types of reports and illustrations that can be assembled from the users input data or from the input data as compiled for a number of users.

FIG. 8 shows an example of web page 800 where the health care professional, or other authorized individuals or organizations, or the user, can view reports and summaries of readings information input by the user. This information can be displayed in the form of electronic graphs and charts and can be summarized in hardcopy in the form of a Patient Synopsis Reports (PSR) 804.

The health care professional, or other authorized individuals or organizations or the user, may choose to display certain variables by making selections from drop down menus for characteristics 834, symptoms 836, intensity 840 and lifestyle 842. Chart 846 shows the values for mood, treatment effectiveness, and intensity variables graphed over a 45-day time frame 830 with a daily frequency 832. One skilled in the art will appreciate that chart 846 may be implemented with a chronological chart, one or more graphs, a histogram or other device used to display data. Histogram 860 shows the symptoms 836 of painful urine and tender breasts and the characteristics 834 of sharpness over a 45-day time frame 830 with a daily frequency 832. Medication usage (not graphed) could also be charted overtime and used to help determine the effectiveness of a single or combination of drugs both in patients and in clinical trials.

According to one aspect of the invention, pain information is graphically played back to the user, a physician or a health care professional. FIG. 8, shows one frame 802 of a time-sequenced set of images that may show how pain has migrated or spread. The time-sequenced images can be generated by a replay generator function 120 (FIG. 1) that displays dynamic changes in the pain over a period of time. The time-lapsed images can show pain intensity and location information over a period of time, and can include color-coded intensity levels indicating increasing pain intensity in addition to pain migration. The time-lapsed images can be generated and viewed using a loop-type player similar to techniques used to display time-lapsed radar images on weather maps. Alternatively, computer-generated images using an anatomically correct image of a person (e.g., with realistic skin tones and the like) can also be used. Separately or simultaneously with the time-sequenced set of images described above, information input by the user can be displayed in charts (e.g. characteristic 424 and symptoms 500) and graphics (e.g. lifestyle 600), that can move dynamically in sync with the time-sequenced set of images. Chart and graph information can also be presented in static form for a fixed period of time, or in synopsis form in which the frequency of specific occurrences over a specified time period is displayed (e.g. breast tenderness was reported 15 days during a 45 day period). Furthermore, the present invention enables the same time-sequenced set of images, and all functionality described above for individual users, to be applied to groups or a select population of users, so that for example the effectiveness of medical intervention can be tracked and studied across a range of users.

In one embodiment of the invention, the play back sequence includes different sounds or sound levels that correspond to the indicated pain intensity. The ability to rapidly view pain migration information in an easy to understand format will aid health care professionals in assessing and diagnosing pain problems experienced by users.

Figure 9:
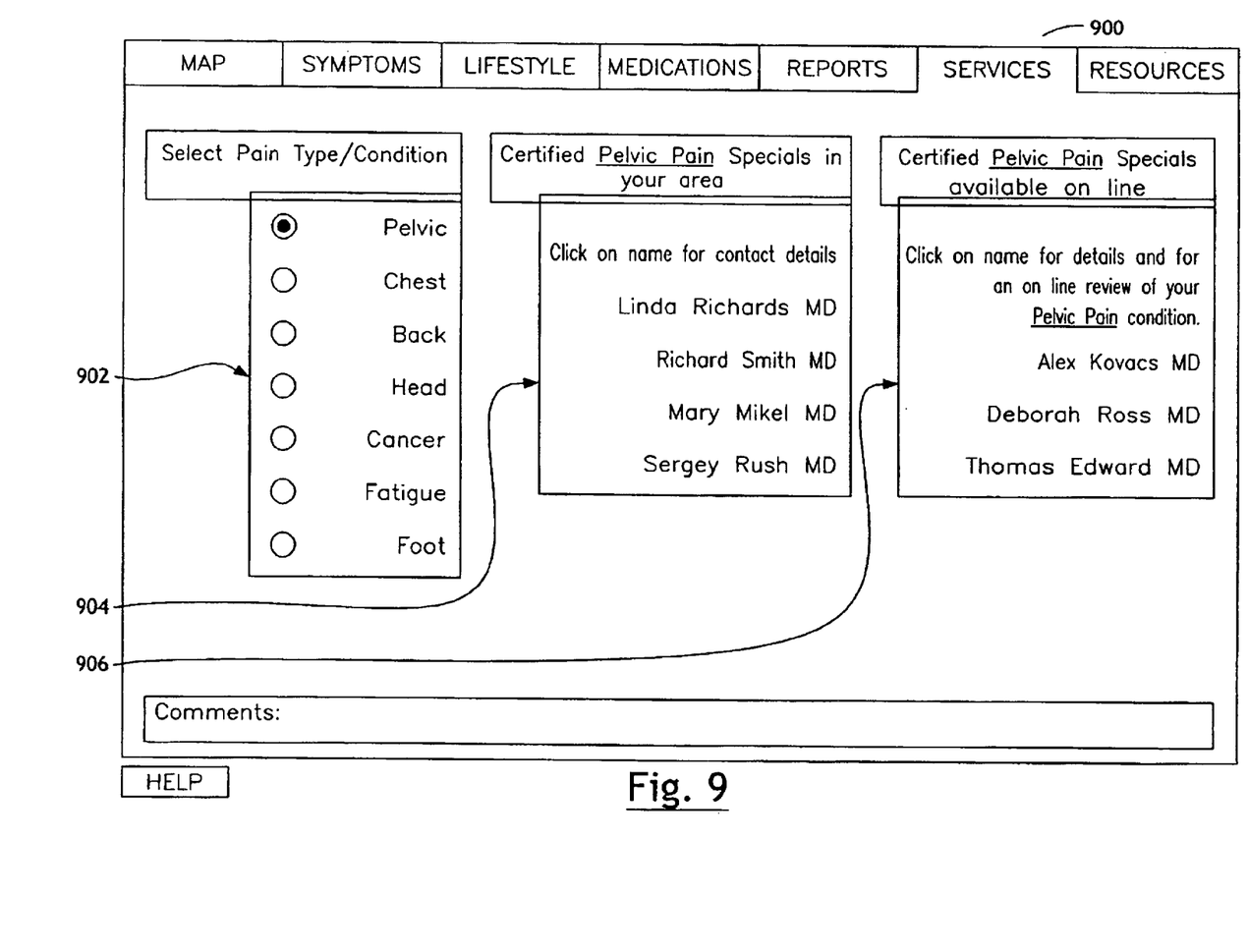
FIG. 9 shows a web page, or other graphical user interface, listing professional services that can be utilized for the type of pain/condition selected.

FIG. 9 shows a web page 900 that includes professional service information that assists users in finding pain specialists based on the type of pain they are experiencing. The user may select a pain type 902 by selecting one of the radio buttons. Based on pain type selected a list of pain specialists with contact information would be provided for both specialists in the users geographically area 904 and specialist that can be contacted through the Internet 906.

Figure 10:
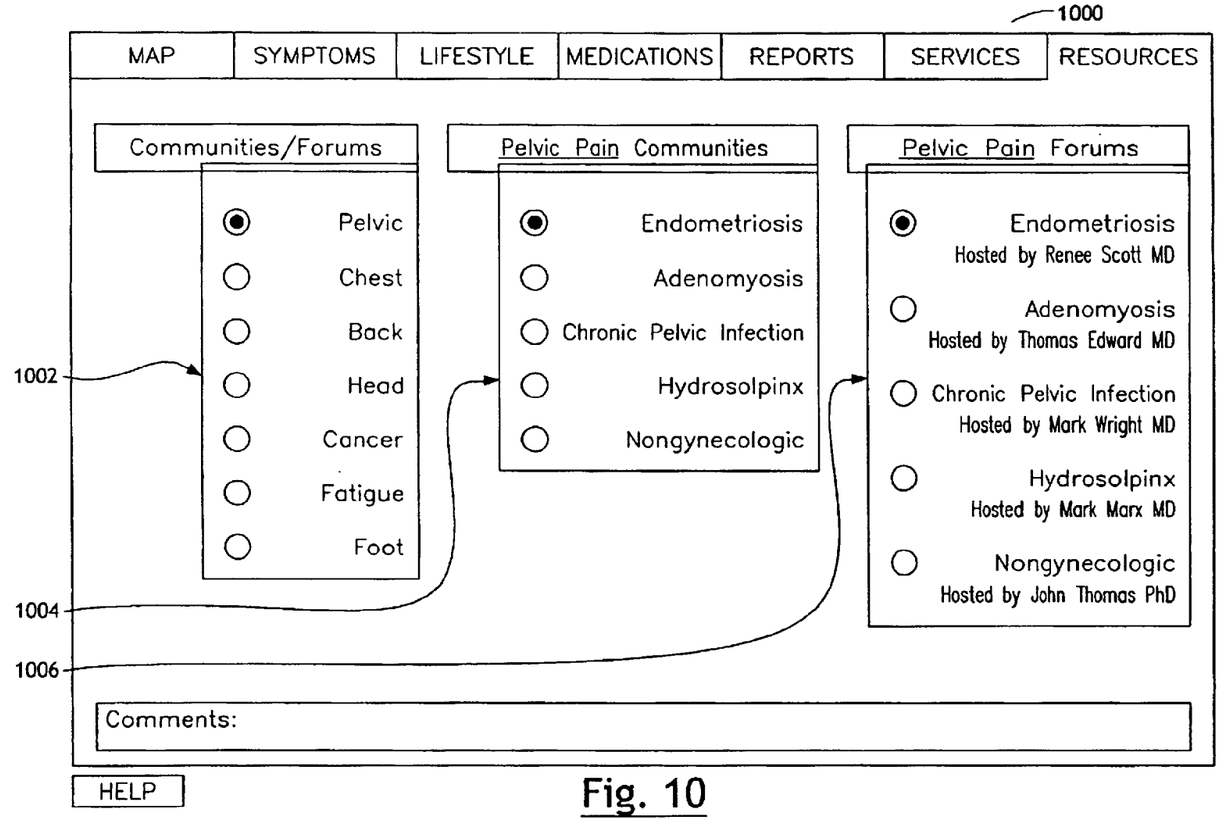
FIG. 10 shows a web page, or other graphical user interface, that lists forums and communities for the type of pain selected.

Finally, FIG. 10 shows web page 1000 that includes links to pain related forums and communities. The user selects the pain type 1002 by selecting on the of the radio button shown in FIG. 10. Based on the pain type selected listing of both communities 1004 and forums 1006 are displayed with the corresponding contact information. This information would provide the user with informational resources such as contacts of support groups that can help assist in any and all treatment plans.

While the present invention has been described in connection with the illustrated embodiments, it will be appreciated and understood that modifications can be made without departing from the true spirit and scope of the invention. For example, information may be entered or displayed with alternative web pages or other mechanisms used to enter or display information.

I claim:

1. A method of obtaining or displaying patient information, comprising the steps of:
   (a) receiving from a first user a first set of medical information describing a medical state experienced by the first user during a first time period;
   (b) receiving from the first user a second set of medical information describing a medical state experienced by the first user during a second time period; and
   (c) displaying a chronological chart related to information obtained with the first and second sets of medical information.

2. The method of claim 1, wherein the first and second sets of medical information are received at a first computer connected to a computer network and transmitted to a pain tracking computer coupled to the computer network.

3. The method of claim 2, wherein the chronological chart is generated by the pain tracking computer at a location different from the first computer.

4. The method of claim 3, wherein the chronological chart is displayed on a web browser and is accessible by a health care professional at a location different from the location of the first user and the location of the pain tracking computer.

5. The method of claim 1, wherein the step of displaying a chronological chart includes showing a chart of at least two variables.

6. The method of claim 5, wherein the at least two variables includes pain characteristics, symptoms, lifestyle and medication.

7. The method of claim 6, wherein pain characteristics include at least one of pressure, throbbing, aching, sharp, and pulling.

8. The method of claim 6, wherein symptoms include at least one of urinating, breast tenderness and bloating.

9. The method of claim 6, wherein lifestyle include at least one of sleep, mood, wellness, and the effectiveness of medical intervention.

10. The method of claim 6, wherein the medication includes at least two different medications.

11. The method of claim 1, further including the steps of:
    (a) obtaining at least one alarm condition; and
    (b) transmitting an alert when at least one of the alarm conditions have been met.

12. The method of claim 11, wherein the at least one alarm condition includes a quantity of medication taken over a period of time.

13. The method of claim 11, wherein the at least one alarm condition includes a pain intensity level.

14. The method of claim 11, wherein the transmitting step includes sending an e-mail message.

15. The method of claim 11, wherein the transmitting step includes sending a page.

16. The method of claim 11, wherein the transmitting step includes sending a phone call.

17. The method of claim 1, further including the step of:

displaying a time-sequenced set of images that illustrates changes in information between the first time period and the second time period.

18. The method of claim 1, further including the steps of:

(d) receiving from a second user a third set of medical information describing a medical state experienced by the second user during the first time period;

(e) receiving from the second user a fourth set of medical information describing a medical state experienced by the second user during the second time period; and wherein step (c) includes displaying a chronological chart related to information obtained with the first, second, third and fourth sets of medical information.

19. The method of claim 18, wherein the chronological chart comprises an aggregate of information obtained from the first user and the second user.

20. The method of claim 1, further including the step of providing feedback to the first user.

21. A computer programmed to perform the steps of:

(a) receiving from a first user a first set of medical information describing a medical state experienced by the first user during a first time period;

(b) receiving from the first user a second set of medical information describing a medical state experienced by the first user during a second time period; and (c) causing a display device to display a chronological chart related to information obtained with the first and second sets of medical information.

22. A computer readable medium containing computer-executable instructions for performing the steps of:

(a) receiving from a first user a first set of medical information describing a medical state experienced by the first user during a first time period;

(b) receiving from the first user a second set of medical information describing a medical state experienced by the first user during a second time period; and (c) receiving from a second user a third set of medical information describing a medical state experienced by the second user during the first time period;

(d) receiving from the second user a fourth set of medical information describing a medical state experienced by the second user during the second time period; and (e) causing a display device to display a chronological chart related to information obtained with the first, second, third and fourth sets of medical information.

23. The computer readable medium of claim 22, wherein the chronological chart comprises an aggregate of information obtained from the first user and the second user.

* * * * *